United States Patent [19]

Klein

[11] 4,059,357
[45] Nov. 22, 1977

[54] DENSITOMETER CALIBRATED REFERENCE STANDARD

[75] Inventor: Gerald L. Klein, Orange, Calif.

[73] Assignee: Beckman Instruments, Inc., Fullerton, Calif.

[21] Appl. No.: 673,026

[22] Filed: Apr. 2, 1976

[51] Int. Cl.$^2$ ............................................. G01J 1/02
[52] U.S. Cl. .................................. 356/243; 356/201; 356/203
[58] Field of Search .............. 356/201, 203, 234, 235, 356/243, 244; 350/314, 172

[56] References Cited

U.S. PATENT DOCUMENTS

| | | | |
|---|---|---|---|
| 2,244,507 | 6/1941 | Thomas | 350/314 X |
| 2,495,778 | 1/1950 | Seifert | 356/203 X |

Primary Examiner—John K. Corbin
Assistant Examiner—Matthew W. Koren
Attorney, Agent, or Firm—Robert J. Steinmeyer; Robert R. Meads; Donald A. Streck

[57] ABSTRACT

A standard for calibrating a densitometer or the like is disclosed consisting of an optically transparent substrate supporting a plurality of spaced bands of different predetermined optical densities. Each band comprises alternate dark and clear strips and is sized to eclipse a beam of light generated in the densitometer and defining an illuminated zone. The width of the clear strips is large compared to the wavelength of the light beam and small compared to the width of the illuminated zone so that the quantities of light passing through the bands as the standard moves through the densitometer, and hence the optical densities of the bands, are directly proportional to the ratio of the areas of the clear strips to the areas of the dark strips in the bands. The bands are placed at an angle to the scan axis of the illuminated zone to present a gradient change in optical density to a scanning densitometer which is within the response time thereof. Additionally, the strips in each band are at an angle to the scan axis to pass across the illuminated zone with an apparent sweeping motion to average out any optical or illumination irregularities across the zone.

5 Claims, 7 Drawing Figures

FIG. 3

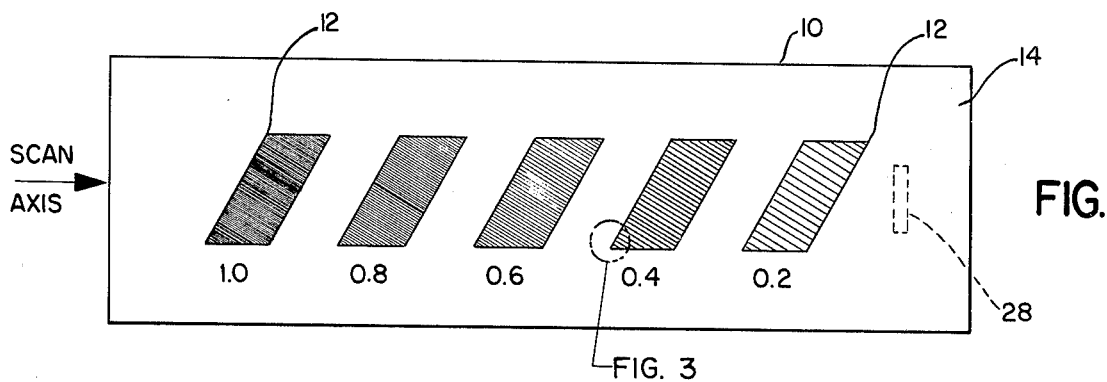
FIG. 1
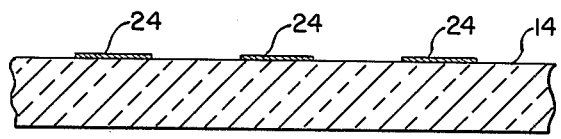
FIG. 2
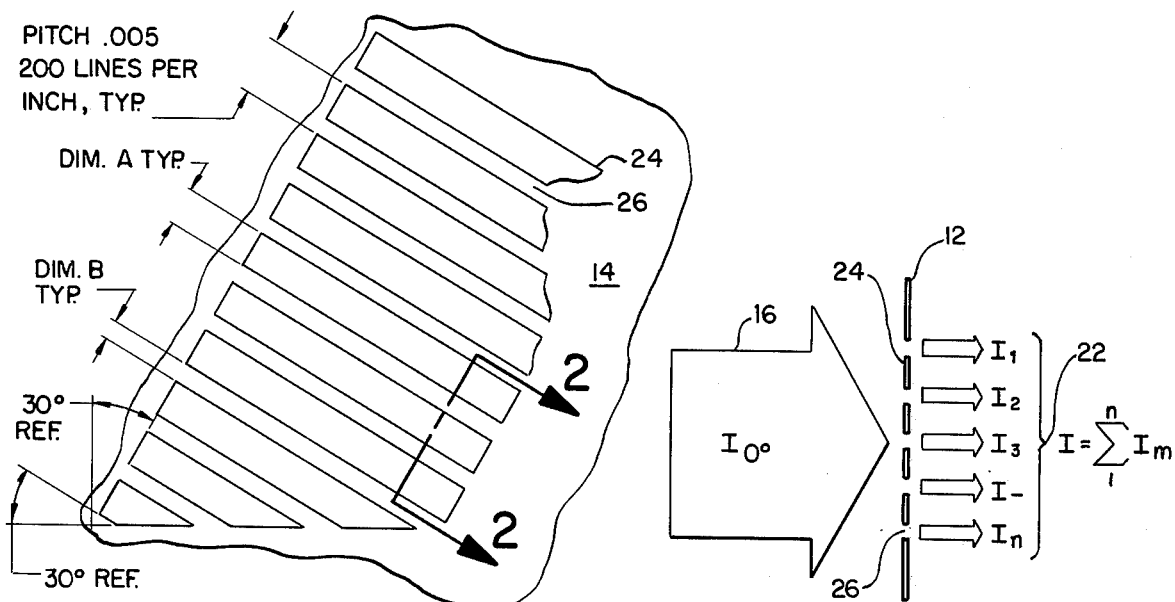
FIG. 3
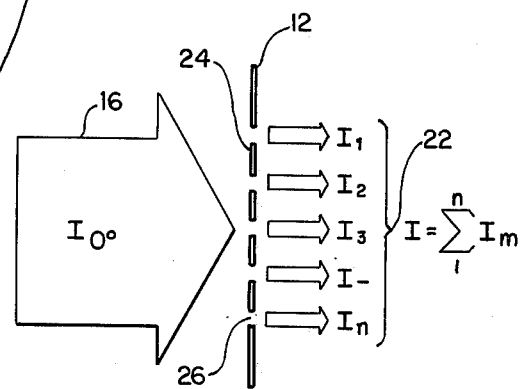
FIG. 4
| BAND | DENSITY – TOL. | %T ± 1% | REL % | DIM. A OPAQUE BAR | DIM. B CLEAR BAR |
|---|---|---|---|---|---|
| 1 | 1.00 ± .02 | 10.0 | 33.3 | .00450 | .00050 |
| 2 | 0.80 ± .02 | 15.85 | 26.7 | .00421 | .00079 |
| 3 | 0.60 ± .01 | 25.1 | 20.0 | .00375 | .00125 |
| 4 | 0.40 ± .01 | 39.8 | 13.3 | .00301 | .00199 |
| 5 | 0.20 ± .007 | 63.1 | 6.7 | .00184 | .00316 |
FIG. 5

DENSITOMETER CALIBRATED REFERENCE STANDARD

BACKGROUND OF THE INVENTION

The present invention relates to the calibration of optical instruments and more particularly to apparatus for calibrating a densitometer or the like.

The use of instrumentation such as the densitometer for measuring optical density is becoming more commonplace in many fields. For example, the assignee of this application has recently developed a dosimeter for use in monitoring the treatment of hyperbilirubinemia in infants by phototherapeutic means. The optical density (a measurement of the ability of a material to transmit light) of the dosimeter changes in response to the equivalent destruction of serum bilirubin in the bloodstream of the infant by light irradiation. Determination of the amount of bilirubin decomposed is dependent upon accurate measurement of the change in optical density of the dosimeter. Numerous federal and state agencies are requiring that means for certifying performance criteria be provided for instrumentation used in such medical diagnoses.

Many materials have the ability to transmit or absorb certain frequencies of light. In the fields of compositional analysis, of which clinical medicine is an important part, this phenomenon has been put to good use. If white light containing the full spectrum of light frequencies is passed through a material sample, the light emerging from the sample will be modified according to the absorptive qualities of the material as to each of the frequencies of the light. Such "filtered" light then can be analyzed, and by comparison to known standards, the composition of the material or presence of specific components can be determined. In a typical scanning densitometer performing the above analysis, the sample, deposited as a thin film on a transparent substrate, is moved along a scan axis and across a zone of illumination in the densitometer. The light passing through the sample is detected and converted to an output signal which may be integrated to eliminate the effects of localized anomalies in the sample film. In this regard, the densitometer generates a chart trace of the output signal during the scanning operation together with a listing of integrated values of the output signal equivalent to areas under the chart trace. Such information enables a skilled technician to draw conclusions concerning the nature of the scanned sample.

Of course, it is important that such densitometers be accurately calibrated and that such calibration be maintained during the operation thereof. Typically, the calibration and testing process comprises causing the densitometer to scan a standard presenting a known optical density equivalent and area. The response of a correctly calibrated and operating densitometer when scanning the standard can be anticipated. By comparing the output of the densitometer scanning the standard to the expected output, the performance of the subject densitometer can be determined and instrument adjustment made to bring the densitometer performance into correlation with the standard.

In the past, such densitometer calibrating standards have been limited by the filter employed therein. In this regard, various filter types are available for incorporation into a standard. However, each has limitations in one or more areas of accuracy, linearity and cost — particularly when it is desired to mass produce calibration standards for use with a widely distributed product line of densitometers or the like.

Ideally, a filter for use in a standard should be accurate. That is, it should present an actual optical density equivalent equal to the intended optical density equivalent. Further, the filter should be producible at low cost in large quantities with uniform filter characteristics. Also the filter should be linear with wavelength. That is, it presents the same optical density equivalent regardless of the wavelength of the light passing therethrough.

SUMMARY OF THE INVENTION

The foregoing as well as other objectives have been achieved by the present invention in which bands capable of totally eclipsing an illuminated zone and comprising light attenuating strips in spaced relationship and displaying a known optical density of light passing therethrough are imposed on an optically transparent substrate. In the preferred embodiment, the bands are angled in relation to the densitometer scan axis and the strips comprising the bands are also angled in relation to the scan axis. The space between the strips is large compared to the wavelength of the light passing therethrough for detection in the densitometer and yet small in comparison to the width of the illuminated zone along the scan axis so that the amount of detected light can be converted by simple mathematics to an optical density equivalent for the band.

DESCRIPTION OF THE DRAWINGS

FIG. 1 is a depiction of a densitometer standard according to the present invention having five bands thereon exhibiting optical densities of 1.0, 0.8, 0.6, 0.4 and 0.2.

FIG. 2 is a cross-section at 2—2 through a portion of the densitometer standard of FIG. 3.

FIG. 3 is an enlarged view of the circled area 3—3 of the densitometer standard of FIG. 1.

FIG. 4 is a depiction of the effect of the bands of the present invention.

FIG. 5 is a table giving dimensions for a tested embodiment of the present invention.

DESCRIPTION OF THE PREFERRED EMBODIMENT

Figure 6:
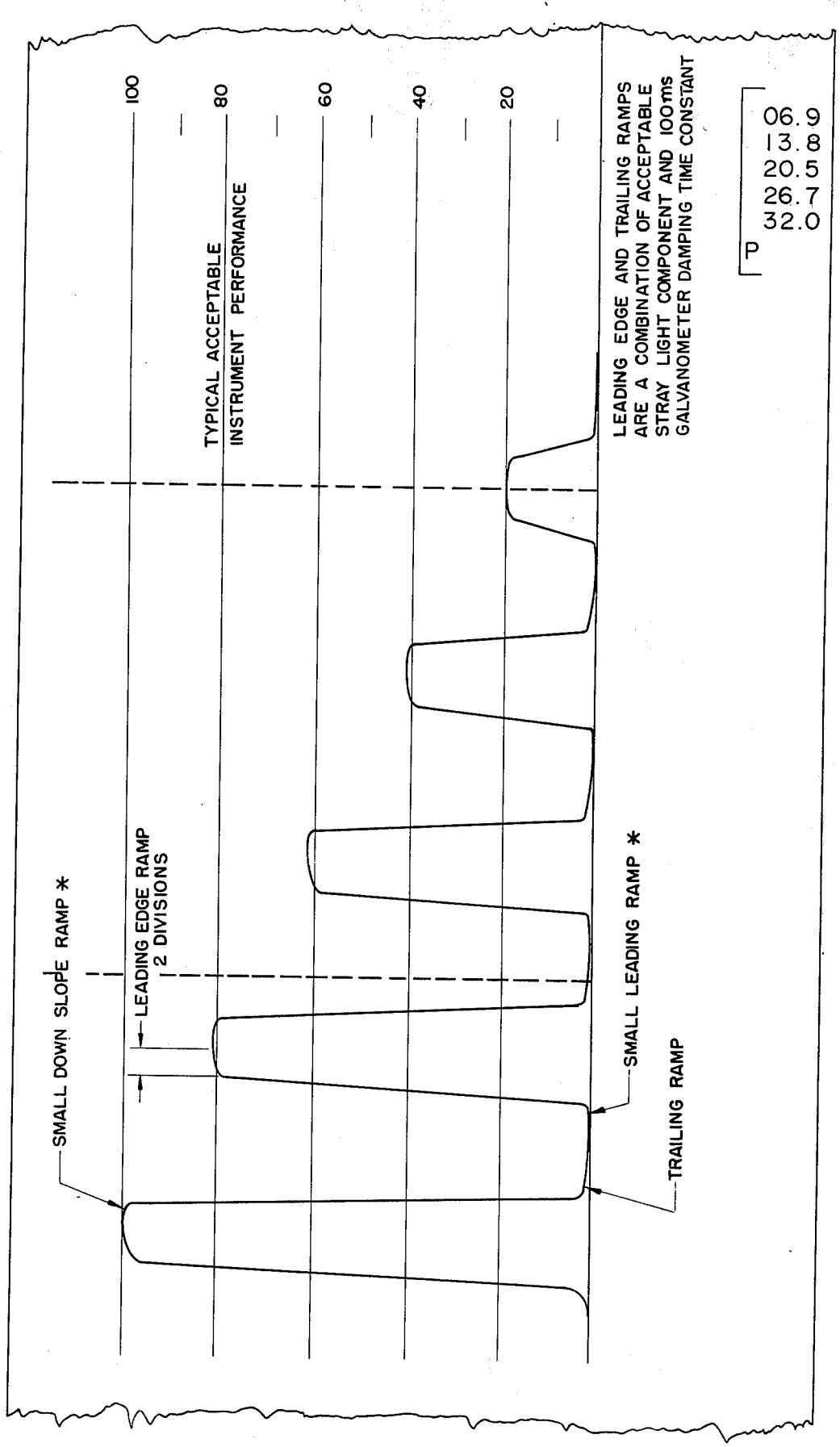
FIG. 6 is the output of a correctly operating densitometer in response to scanning a standard according to the present invention.

A densitometer standard 10 made according to the present invention is shown in FIG. 1. Densitometer standard 10 comprises a series of bands 12 of different predetermined optical density imposed on an optically transparent substrate 14. The substrate 14 may be any suitable homogeneous transparent material such as glass, plastic film, etc. The bands 12 may be photographically developed emulsions or chemically etched films such as chromium, and, ideally, should be as a thin film on the surface of the substrate 14 as shown in FIG. 2.

The bands 12 of densitometer standard 10 are shown in greater detail in FIG. 3. The bands 12 are precision microimages of alternate dark light-attenuating strips 24 and clear strips 26. For best performance, the light-attenuating strips 24 should be of an optical density in the range of 3.3 or greater. If an illumination zone generated in a densitometer is imposed upon the bands 12 such that the illuminated zone is totally eclipsed within the overall perimeter of a band 12, then the amount of light which passes through the band becomes directly proportional to a ratio of the width or area of the light-attenuating strips 24 to the width or area of the clear or open strips 26.

The operation of the bands 12 in the present invention is depicted in FIG. 4. If the incident light ($I_0$) 16 is passed through a band 12 having dark strips 24 and clear strips 26, the incident light 16 will be broken up into a number of small segments 22 indicated as $I_1$-$I_n$. The effective transmitted light is given by the formula:

$$I = \sum_{1}^{n} I_n$$

The equivalent optical density is then expressed as:

$$OD = \text{LOG}_{10} \frac{I_0}{I}$$

If the width of the clear strips 26 is large compared to the wavelength of light passing therethrough and small in comparison to the width along the scan axis of the illuminated zone, then the transmitted light can be converted by simple mathematics to percentage of incident light and, further, to an equivalent optical density according to the above equations. The dimensions of the bands 12 as manufactured, tested and hereinafter described have been carefully calculated to yield the following optical density equivalents: 1.0, 0.8, 0.6, 0.4 and 0.2.

As depicted most clearly in FIGS. 1 and 3, it is desirable to angle the bands 12 (preferably between 30° and 60°, measured forward or backward) relative to the scan axis of the densitometer and to angle the dark strips 24 and clear strips 26 in the same range in relation to the same scan axis. This creates sweeping action by both the bands 12 and the strips 24, 26 across the illuminated zone along a line normal to the scan axis so as to neutralize the effects of any irregularities in the illuminated zone and to ensure that the response time of the densitometer is not exceeded as it scans the standard of the present invention.

In the later regard, it is common for scanning densitometers to include delay circuit for stabilizing the outputs thereof. Under such conditions, if a very rapid or step function change were to occur in the optical density of a sample being scanned, the output of the densitometer would change slowly over the response time of the delay circuits toward a new value corresponding to the new optical density of the sample. If the new value were achieved before the sample being scanned changed again in optical density, the densitometer output would be correct in quantity even though a slight delay between change and full response occurred internally. If, on the other hand, the optical density of the sample being scanned again changed before the new value was achieved, the output circuitry would attempt to achieve the value of the latest input without attaining the first value and the resultant densitometer output would be incorrect. In the latter case, the response time of the densitometer was exceeded.

In the illustrated form of the standard of the present invention, placing of the bands 12 at a 30° to 60° angle to the scan axis causes the bands to sweep across the illuminated zone along a line normal to the scan axis rather than subject the densitometer to a rapid or step change in optical density. Such action may be appreciated by referring to FIG. 1 wherein a typical illuminated zone 28 is shown in relation to densitometer standard 10. As represented, as densitometer standard 10 is moved across the illuminated zone 28, each band 12 will move along the scan axis. If the illuminated zone 28 is perpendicular or normal to the scan axis as shown, as an angled band 12 moves across illuminated zone 28 from left to right along the scan axis, the illuminated zone 28 will be gradually covered by the band 12 from the top down. As the band 12 continues to move across the illuminated zone 28, the illuminated zone 28 will remain totally eclipsed for a period of time and then be gradually uncovered from the top down. This gradual covering and uncovering or sweeping of the illuminated zone 28 along a line normal to the scan axis replaces the step function change in optical density created by a vertical band, with a gradient change in optical density within the response time of the desitometer. This assures that the response time of the densitometer will not be exceeded.

With regard to possible irregularities in the illuminated zone, the source of illumination in a scanning densitometer is normally an incandescent bulb having a helically wound filament. This can create small differences in the amount of light at various points in the illuminated zone 28. Irregularities in the optical system creating the illuminated zone 28 can also cause non-homogeneous illumination across illuminated zone 28. If bands 12 moved across the illuminated zone 28 with strips 24, 26 parallel to the scan axis, only those portions of the illuminated zone 28 under clear strips 26 would be sensed. This could cause a slightly distorted response depending on the nature of the illuminated zone 28 at these points. By referring to FIG. 1, it can be visualized how, as the densitometer standard 10 moves across the illuminated zone 28 from left to right, the angle of the strips 24, 26 will produce a sweeping motion of the strips 24, 26 across the zone 28 from the bottom toward the top along a line normal to the scan axis in the same manner as the angle of bands 12 produces a sweeping of the bands 12 from the top down as the illuminated zone 28 is covered and uncovered during the scanning operation. This apparent sweeping motion assures that all of illuminated zone 28 will be detected by the scanning apparatus of the densitometer (not shown) and not just selected portions. Thus, the apparent sweeping motion of strips 24, 26 averages out any optical and illumination irregularities across the illuminated zone 28.

In a densitometer it is common practice that the ambient or starting condition be set at a zero level. Then, if the scan of a sample begins and ends on the substrate supporting the sample, the optical density of the substrate is considered to be the ambient and is ignored. Under such circumstances, any change during the scan is a function of the sample alone and the media of the substrate does not enter into the calculations made by the densitometer. In the standard 10 of the present invention, the optical densities of the bands 12 present the only changes in optical density on the substrate 14 and are a function of geometry alone. Therefore, when the standard 10 is scanned by starting and stopping on the substrate, each band 12 presents a different yet constant optical density equivalent regardless of the wavelength of the light passing therethrough.

Referring to FIG. 3 and FIG. 5, the construction of bands 12 as employed in a preferred embodiment of the present invention is shown in greater detail. In this regard, however, please bear in mind that while the dimensions and angles shown by FIG. 3 in conjunction with the accompanying table of FIG. 5 are preferred for a particular embodiment, other combinations of angles and sizes may be selected to meet different specific requirements of particular densitometers, spectrophotometers, colorimeters, or the like. In particular, the scan rate of the instrument determines the range of angles of the bands 12 which will prevent an exceeding of the response of the associated densitometer. In a similar manner, the angle of the band 12 and the dimensions of the illuminated zone of the instrument will determine the optimum angle for strips 24 and 26 in sweeping across the illuminated zone.

Further, the pitch or distance between dark strips 24 should be chosen to minimize distortion. In this regard, if a large pitch is employed, the effect is a series of bright and dark strips moving across the scanner. Moreover, since a glowing helical filament light source is most often employed in densitometers, if the pitch is large, the filament itself will appear as brighter and less bright areas within the clear strips 26. On the other hand, if the pitch is too small, diffraction effects of narrow clear strips 26 will become significant. In other words, some of the light rays will partially bend away from an angle of incidence normal to the scanner so that the light received by the scanner will not be according to the calculated value. Ideally, the pitch should not be less than approximately 10 times the wavelength of the incident light in order to eliminate significant diffraction effects. With incandescent light this is about 0.003 inches or 333 strips per inch maximum.

Figure 7:
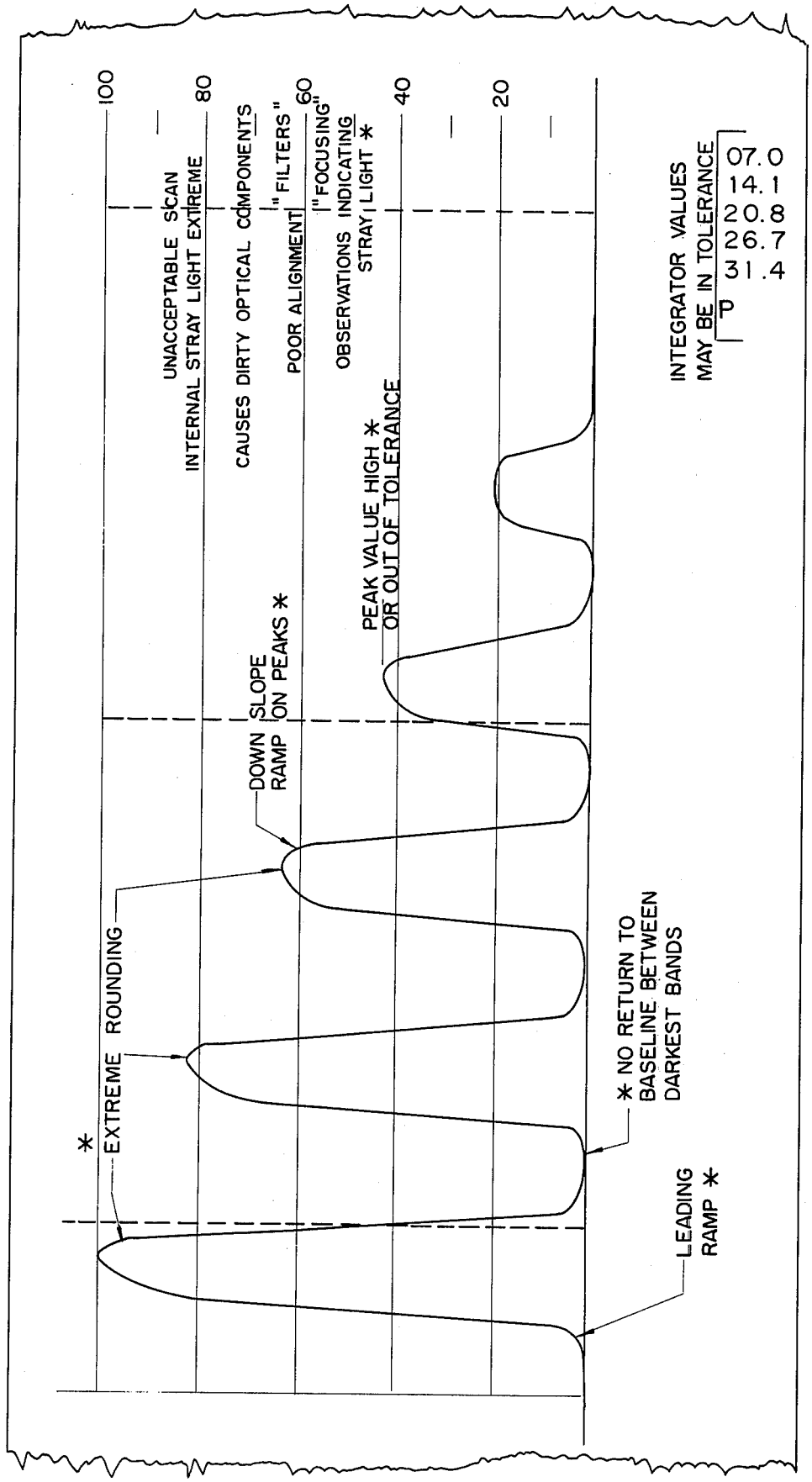
FIG. 7 is the output of an incorrectly operating densitometer in response to scanning a standard according to the present invention.

The use of the standard 10 in checking the performance of a scanning densitometer can best be understood with reference to FIGS. 6 and 7 wherein actual densitometer outputs produced by scanning a densitometer standard 10 as described herein are depicted. Referring first to FIG. 6, the output from an acceptable operating instrument is shown. Scanning the series of five bands 12 yields a chart showing five peaks with flat tops. The shape shows the gradual rise, period of eclipse, and gradual fall produced by the angle of bands 12. The slight ramps at the tops and bottoms of the leading and trailing edges are a function of the response time described earlier.

Since optical density (O.D.) is the logarithm of 1/T where T is transmittance of light, if a logarithmic recorder is used and the 1.0 band is set to read 100%, densitometer linearity can be checked. On the chart of FIGS. 6 and 7, 100% on the chart corresponds to 1.0 O.D., 80% to 0.8 O.D., 60% to 0.6 O.D., 40% to 0.4 O.D. and 20% to 0.2 O.D. As can be seen, when the densitometer producing the output of FIG. 6 scanned the standard 10 of FIG. 1 having bands 12 of effective optical densities 1.0, 0.8, 0.6, 0.4 and 0.2, the output was substantially linear as shown by the peaks at 100, 80, 60, 40 and 20%.

Next, since the size of the zone of illumination is fixed and if the bands 12 are a very accurate and equal width, the areas traversed by the zone will be the same for each band 12. Weighing this area by the optical density equivalent for each band will then yield relative percent values for each of the bands. The relative percent values will be directly proportional to the areas under the curves on the scan chart. For example, for the standard of FIG. 1 used to produce the output of FIG. 6, the sum of the optical density equivalents of the bands (1.0 + 0.8 + 0.6 + 0.4 + 0.2) equals 3.0. Thus, the portion of the intergrated total attributable to the 1.0 O.D. band is 1.0/3.0 or 33.33%. Likewise the 0.8 O.D. band is 0.8/3.0 or 26.66%. In the same manner the remaining bands represent 20.00, 13.33 and 6.66% respectively. The printouts of 32.0, 26.7, 20.5, 13.8 and 06.9 represent the integrated values calculated by the densitometer and would be considered to be within acceptable limits.

By contrast, refer to FIG. 7 which shows a densitometer output of questionable acceptability produced from the same standard. The change in output was caused by the insertion of an unclean optical filter. Maladjustment or malfunctioning parts may cause an even more pronounced deviation from the acceptable output of FIG. 6 which may be easily recognized as unacceptable and alert the operator to the need for corrective action before the instrument was used further.

It is to be understood that while the alternate dark and clear strips 24 and 26 are shown as straight, equally spaced, and parallel, this is the preferred embodiment thereof. Bands 12 comprised of curved or patterned alternate dark and clear strips providing a sweeping action across the illuminated zone also may be employed in the standard of the present invention.

Having thus described my invention, I claim:

1. A wavelength independent optical density standard for use in calibrating and checking an instrument which scans the standard with an illuminated zone along a predetermined scanning axis, the standard comprising:
   a. an optically transparent substrate; and,
   b. a light attenuating material imposed on said substrate to create a plurality of light attenuating strips in spaced relationship to form a band displaying a known optical density to light passing therethrough, said band having an area capable of totally eclipsing the illuminated zone, said light attenuating strips being disposed to produce a sweeping motion of the illuminated zone along a line normal to the scanning axis as the standard is scanned.

2. The optical density standard of claim 1 wherein:
   said band is disposed to produce a sweeping motion of the illuminated zone along a line normal to the scanning axis as the standard is scanned.

3. A wavelength independent optical density standard for use in calibrating and checking an instrument which scans the standard with an illuminated zone along a predetermined scanning axis, the standard comprising:
   a. an optically transparent substrate; and,
   b. a plurality of bands disposed on sid substrate and spaced along the scanning axis, said bands each displaying a different predetermined optical density equivalent to light passing therethrough, said bands each comprising a plurality of light attenuating strips in spaced relationship, said bands each having an area capable of totally eclipsing the illuminated zone, said strips and said bands each being independently angled with respect to the scanning axis an amount sufficient to produce a sweeping motion across the illuminated zone by a portion of each of said strips and bands along a line normal to said scanning axis.

4. The optical density standard of claim 3 wherein:
   said band and said strips assume independent acute angles to the scanning axis.

5. The optical density standard of claim 4 wherein:
   said angle of said band and said angle of said strips to the scanning axis is in the range of between 30° and 60°.

* * * * *